United States Patent [19]
Sturman et al.

[11] Patent Number: 6,076,018
[45] Date of Patent: Jun. 13, 2000

[54] METHOD AND APPARATUS FOR LOW POWER REGULATED OUTPUT IN BATTERY POWERED ELECTROTHERAPY DEVICES

[75] Inventors: Andy Sturman; Thomas Grey, both of Carlsbad, Calif.

[73] Assignee: Woodside Biomedical, Inc, Carlsbad, Calif.

[21] Appl. No.: 09/148,837

[22] Filed: Sep. 4, 1998

[51] Int. Cl.[7] .................................................. A61N 1/32
[52] U.S. Cl. .................................... 607/72; 607/74; 607/2
[58] Field of Search ............................... 607/4, 5, 2, 11, 607/7, 46, 48, 39–42, 72, 74

[56] References Cited

U.S. PATENT DOCUMENTS

| | | | |
|---|---|---|---|
| 4,016,473 | 4/1977 | Newman | 320/14 |
| 4,024,875 | 5/1977 | Putzke | 128/419 |
| 4,096,866 | 6/1978 | Fischell | 128/419 |
| 4,274,132 | 6/1981 | Molyneux-Berry | 363/21 |
| 4,868,730 | 9/1989 | Ward | 363/21 |
| 4,907,602 | 3/1990 | Sanders | 128/787 |
| 4,926,864 | 5/1990 | Dufresne et al. | 128/421 |
| 4,981,146 | 1/1991 | Bertolucci | 128/802 |
| 5,021,758 | 6/1991 | Lane | 333/245 |
| 5,065,083 | 11/1991 | Owens | 320/13 |
| 5,101,335 | 3/1992 | Ludden et al. | 363/21 |
| 5,218,960 | 6/1993 | Privas | 128/423 |
| 5,369,364 | 11/1994 | Renirie et al. | 324/430 |
| 5,391,193 | 2/1995 | Thompson | 607/29 |
| 5,397,338 | 3/1995 | Grey et al. | 607/115 |
| 5,631,534 | 5/1997 | Lewis | 320/6 |
| 5,658,319 | 8/1997 | Kroll | 607/7 |
| 5,735,884 | 4/1998 | Thompson et al. | 607/36 |
| 5,744,931 | 4/1998 | Arai et al. | 320/43 |
| 5,757,629 | 5/1998 | Yntema et al. | 363/21 |
| 5,772,689 | 6/1998 | Kroll | 607/4 |
| 5,774,424 | 6/1998 | Yoo | 368/10 |
| 5,800,461 | 9/1998 | Menken et al. | 607/7 |
| 5,871,505 | 2/1999 | Adams et al. | 607/5 |
| 5,913,877 | 6/1999 | Kroll et al. | 607/7 |
| 5,959,371 | 9/1999 | Dooley et al. | 607/5 |
| 5,974,339 | 10/1999 | Baker, Jr. et al. | 607/7 |

FOREIGN PATENT DOCUMENTS 0 779 068 A1  11/1996  European Pat. Off. .

*Primary Examiner*—Kennedy Schaetzle
*Attorney, Agent, or Firm*—K. David Crockett, Esq; Crockett & Crockett

[57] ABSTRACT

A device for controlling the discharge of a battery supplying an intermittent load, such as a nerve stimulation device. The device includes a controller which operates a switched inductor to feed a capacitor with numerous small pulses from the battery, thereby building up the charge and voltage on the capacitor, and occasionally discharging the capacitor to a load. The capacitor discharge is at a higher current than the small pulses from the battery, so the battery is drained at small instantaneous discharge rates compared to the high instantaneous discharge current from the capacitor.

9 Claims, 3 Drawing Sheets

METHOD AND APPARATUS FOR LOW POWER REGULATED OUTPUT IN BATTERY POWERED ELECTROTHERAPY DEVICES

FIELD OF THE INVENTION

The present invention relates generally to the field of battery powered devices. More specifically, the present invention relates to battery powered electrotherapy devices such as non-invasive nerve stimulation devices, Transcutaneous Electrical Nerve Stimulator (TENS) devices, muscle stimulators, etc.

BACKGROUND OF THE INVENTION

Portable electrotherapy devices typically utilize a relatively small battery to power internal circuitry which, in turn, provides an output in the form of an electrical signal. The electrical signal output of such devices has been shown to have therapeutic benefit to a patient for a wide variety of medical conditions. These devices have been described as non-invasive nerve stimulation devices, electro-acupuncture devices, and in acupuncture terminology stimulate an acupuncture point.

Portable electrotherapy devices are most conveniently powered by coin cell or button cell batteries such as those used for hearing aids, calculators and other small consumer electronic devices. Through pulse generating circuits, these devices may deliver thousands of pulses per hour from the battery. For example, an electrical pulse repetition rate of approximately 70 pulses per second and a pulse width of 80 microseconds have been found to provide effective relief of nausea. Hundreds of thousands to millions of pulses may be required to treat long lasting nausea, as may be required for post operative nausea, chemo-therapy nausea and other long lasting nausea conditions.

These electrotherapy devices provide a variety of pulse amplitude variations and combinations, or bursts of pulses at specific intervals. For example, the electrical pulse pattern used in our ReliefBand® electrotherapy product comprises about 350 microsecond pulse width at about 31 pulses per second at power levels of about 10–35 milliamps peak pulse height. A wide range of pulse patterns may be used in noninvasive nerve stimulation devices.

Other electrotherapy devices are designed for Functional Electrical Stimulation (FES), which exercises muscles near the point of stimulation. Transcutaneous Electrical Nerve Stimulation (TENS) inhibits sensory nerve communications in the area of stimulation to block pain. All these battery powered electrotherapy devices are characterized by a stimulation output, typically in the form of a voltage or current pulse delivered at a particular pulse shape and waveform. The pulse amplitude, pulse width, and pulse frequency are selected so as to be suitable for treating particular symptoms or conditions such as pain, addiction, nerve disorder, muscle disorder, organ malfunction, etc. Patients using these devices receive direct benefit through the improvement of their quality of life.

The energy needed to deliver the stimulation output is delivered from a battery supply, which may consist of one or more battery cells at a particular nominal voltage and particular battery chemistry. Our ReliefBand® electrotherapy device uses coin cell batteries of standard size, which are readily available. The stimulation output peak pulse amplitude is commonly in a range of 1 to 100 milliamps, which is delivered for a particular time depending on the pulse waveform.

Many types of batteries suitable for use in battery powered electrotherapy devices are optimized to deliver electrical current at lower loads than the required stimulation output. For example, a typical coin cell battery may be rated to provide 0.1 to 0.3 milliamps of current for 100 minutes if the battery is drawn down at an average electrical current draw of 0.1 to 0.3 milliamps.

As a result of the discrepancy between the optimal current draw on the battery and the current draw required for therapeutic pulses, the battery is not used optimally and battery performance and battery life are degraded. Because of battery chemistry, the overall amount of power that can be drawn from a battery is smaller for large current drains than for small current drains. A battery may be able to provide 0.02 milliamps for 100 minutes, but may only provide current of 0.1 milliamps for 10 minutes (instead of 20 minutes), so that half the battery power is lost if the current is drawn off rapidly. Moreover, the problem becomes even greater as the current draw is increased. Thus, drawing current at the rate of 1 milliamp will not provide the expected 1 minute of current (at an expected half power loss), but will provide far less, perhaps only a small fraction of a minute of current at 1 milliamp. For example, if a battery is discharged for a 10 millisecond pulse of 1 milliamp every second, the average current draw is 0.01 milliamps, but the battery will be depleted according to the instantaneous current of 1 milliamp, not the average current of 0.01 milliamps. Rather than obtaining 100 minutes of operation, the battery will provide far less current and power. If, however, the battery is discharged at 0.02 milliamps for a 0.5 second pulse every second, the average current draw still is 0.01 milliamps, but the battery will last according to the instantaneous current draw of 0.02 milliamps. The battery will provide 100 minutes of current when drawn down in this manner.

Battery powered electrotherapy devices usually require a higher voltage therapeutic output pulses than can be provided by conveniently available batteries. Accordingly, electrotherapy devices typically use a transformer to step up the pulses from the battery output to the higher voltage output required for therapeutic devices. The high voltage output is required to allow the pulsed electrical current to be delivered to a particular electrical load, for example, living tissue. The electrical impedance of human skin can be modeled as a 500 ohm resistance. Accordingly, if the device is to deliver 30 milliamps into the skin, then it needs to provide a 15 volt output across the skin.

In a conventional electrotherapy device, a transformer is typically connected to the battery, either directly or through a switching mechanism, and the voltage output from the transformer is proportional to the battery voltage. A problem occurs when the battery voltage begins to lower as the battery becomes depleted. Because the high voltage output is proportional to the battery voltage, the output voltage capability lowers and eventually the electrical current output also lowers for a given electrical load. When the current output lowers, the device's therapeutic effectiveness is lessened.

This problem is a serious problem for patients who use electrotherapy devices for chronic conditions. The patient may experience a lower quality of life, and possibly a degradation in health, as the device's therapeutic effectiveness diminishes over time. The device may provide a low battery indicator, but effectiveness may still be diminished. The device may also just shut off if the battery becomes too depleted, at which point the individual is left without the therapeutic benefit of the device with no adequate warning to allow for a replacement device or battery supply to be obtained. Moreover, current electrotherapy devices do not manage battery consumption so as to obtain the maximum available amount of power from the battery. This leads to more frequent battery replacements than would be required if the battery power could be managed more effectively.

Various circuits have been proposed for use in monitoring charge remaining on a battery, or to generate a pulse from a battery for use in an electrotherapy device. A number of devices have used methods for measuring remaining battery capacity directly for implanted devices e.g., Renirie et al., U.S. Pat. No. 5,369,364, Schmidt, U.S. Pat. No. 5,369,364, Arai, U.S. Pat. No. 5,744,393, Thompson, U.S. Pat. No. 5,391,193. These methods may include switching to an alternative power source e.g., Fischell, U.S. Pat. No. 4,096, 866, or disabling the therapeutic output on a low battery condition, e.g., Putzke, U.S. Pat. No. 4,024,875, but do not address the regulation of the stimulation output as the battery is depleted.

Privas, U.S. Pat. No. 5,218,960, describes a low battery voltage detector for stopping stimulation pulse generation when the battery is too low, but that method requires a prior knowledge of the low battery cutoff voltage so that the circuit component values can be set accordingly. Privas does not address the problem of the therapeutic output voltage lowering as the battery voltage lowers to the cutoff value, thereby decreasing the therapeutic value of the output. Also, Privas does not provide the individual with adequate warning of the pending low voltage condition and cessation of therapeutic output, rather, the output is stopped and the low battery signal is given at the same time.

Dufresne et al., U.S. Pat. No. 4,926,864, describes a circuit for generating a high voltage and monitoring that high voltage through circuit feedback to maintain the high voltage within a specified range as the battery supply is depleted. The Dufresne et al. method suffers in that the charging pulse width in the high voltage generator must be lengthened as the battery supply is depleted. This causes an increase in power consumption that Dufresne et al. address by limiting the charging pulse width to a maximum value. As a consequence, the Dufresne et al. method cannot dynamically adjust the monitored high voltage generator to take advantage of the full range of battery supply capacity. Further, Dufresne et al. makes no provision for adequately warning the patient of the remaining battery life when their control circuit switches to a lengthened pulse width.

Owens, U.S. Pat. No. 5,065,083, describes a system for monitoring the battery voltage and decreasing the output power to allow the system to operate at lower battery voltage as battery power decreases during normal use. The Owens method suffers in that output power must be decreased, rather than maintained at a constant, therapeutic level. Although Owens provides for a low battery indicator, the only indication given is that the output has been decreased. It does not provide for any indication of remaining battery life.

SUMMARY OF THE INVENTION

The battery discharge circuit of the present invention is designed to enhance the battery life of battery powered electrotherapy devices. An electronic pulse generator limits peak current draw from a battery supply so as to extend the battery life. It maintains a constant therapeutic pulse output to the patient as the battery supply is depleted, even as the battery output voltage declines. The pulse generator accomplishes this by discharging the battery into an intermediate storage device at optimal discharge rate, storing the current in this device and periodically discharging the stored current in a high current, short pulse width therapeutic pulse output. So far as the battery is concerned, it sees a peak current draw in its optimal range, but so far as the patient is concerned, the patient feels a therapeutic pulse that far exceeds the optimal current draw for the battery. The therapeutic output pulse may also be converted to a voltage several times higher than the battery voltage. The circuit may also provide the patient with a low battery warning with adequate time to obtain a replacement device or replacement battery source while maintaining a consistent therapeutic output pulse to the patient.

The battery discharging circuit is described in connection with its use in an electrotherapy device. However, the method of discharging the battery at low average current by pulse charging a capacitive storage unit may be employed in various other environments where high current intermittent loads are powered by a battery. For example, flashing safety lights, intermittently operating electrical motors such as those used on power tools, battery operated defibrillators, etc. may be powered by batteries through the circuitry described below to obtain extended battery life.

DETAILED DESCRIPTION OF THE DRAWINGS

Figure 1A:
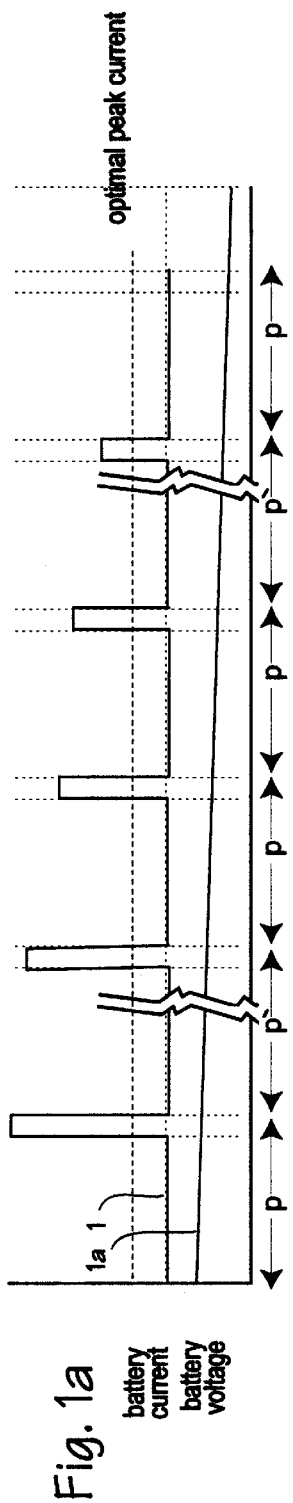
FIG. 1a is a pulse diagram for an electrotherapy device pulse generator without a controlled battery draw.
Figure 1B:
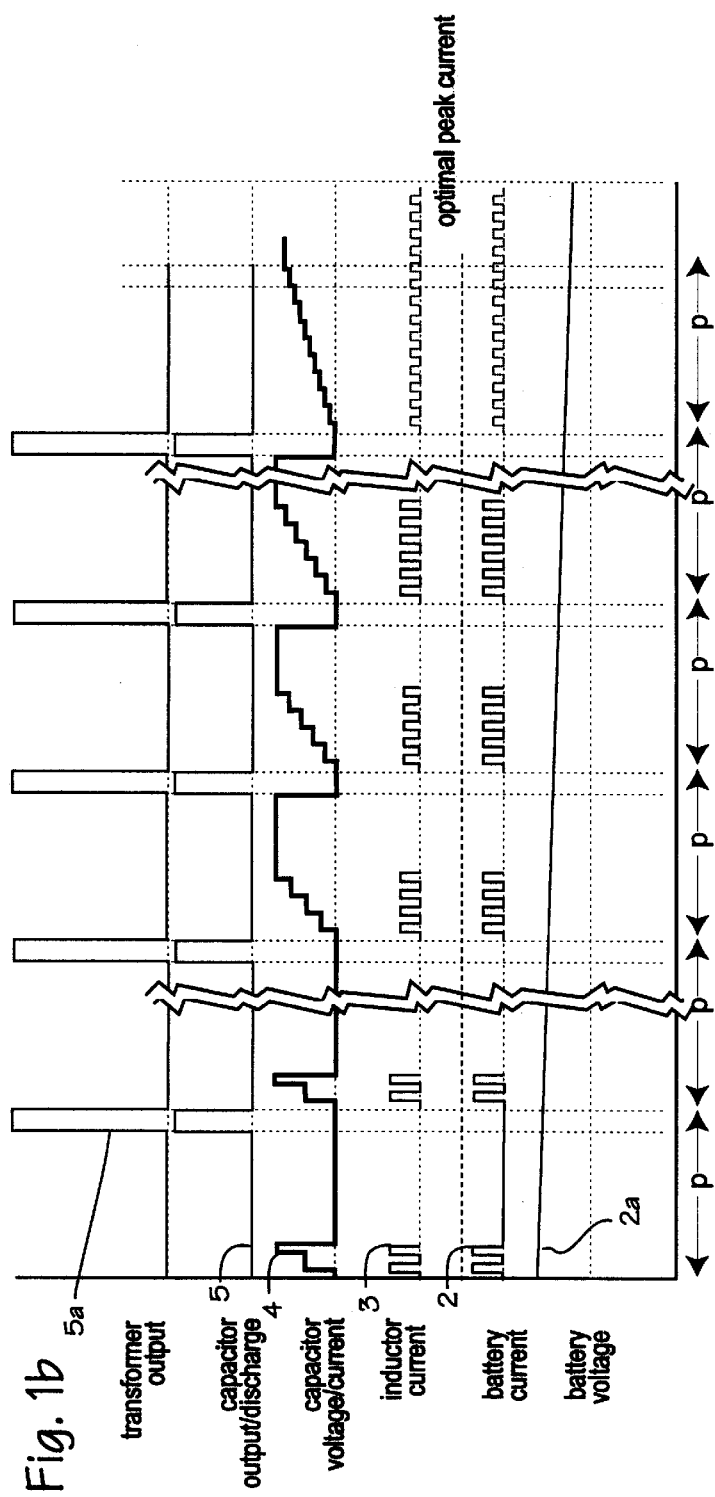
FIG. 1b is a pulse diagram for an electrotherapy device pulse generator with a controlled battery draw.

FIG. 1a is a pulse diagram for an electrotherapy device pulse generator without a controlled battery draw. Here, a battery is discharged once during each pulse period and at a high amplitude for each corresponding therapeutic pulse sent to the patient. As shown by battery discharge line 1, the pulse amplitude exceeds optimal peak current for the battery. The battery voltage, indicated by the battery voltage line 1a, declines steadily as the battery is depleted. The number of pulses that may be obtained in this system is small compared to the number of pulses that may be obtained with pulses at the optimal current. By contrast, FIG. 1b is a pulse diagram for an electrotherapy device pulse generator with a controlled battery draw. The pulse generator limits the current drawn on the electrotherapy device's battery supply, thus preserving the life of the battery, by discharging the battery in multiple small amplitude pulses. As shown by battery discharge line 2, many discharges at the optimal current draw are created in the pulse period p. These battery discharges are sent to and stored in a switched inductor that in turn discharges pulses to a storage capacitor with pulses indicated by inductor output line 3. The current from the inductor is sent to the capacitor, and charges the capacitor according to the capacitor voltage (or current) status line 4. The storage capacitor stores the switched inductor discharge pulses until commanded to discharge to create a therapeutic pulse. When the capacitor is discharged, it creates a pulsed output pulse indicated by capacitor output (discharge) line 5. The voltage output of the capacitor may be stepped up by a transformer, for example, to provide the desired output level of the therapeutic pulses. The transformer output is shown at line 5a. The pulse discharged from the storage capacitor is the desired battery current discharge amplitude created by an accumulation of optimal current discharge pulses from the battery. The capacitor discharge pulses are maintained at constant voltage, even as the battery voltage drops, as indicated by battery voltage line 2a. The battery voltage also declines at a much lower rate compared the direct discharge system illustrated in FIG. 1a.

Essentially, instead of drawing one large pulse out of the battery when a therapeutic pulse is needed to be sent to the patient, the electrotherapy device pulse generator characterized in FIG. 1b draws a series of smaller pulses, each of optimal pulse amplitude, which accumulate and are stored to be discharged when a therapeutic pulse is needed to be sent to the patient.

Figure 2:
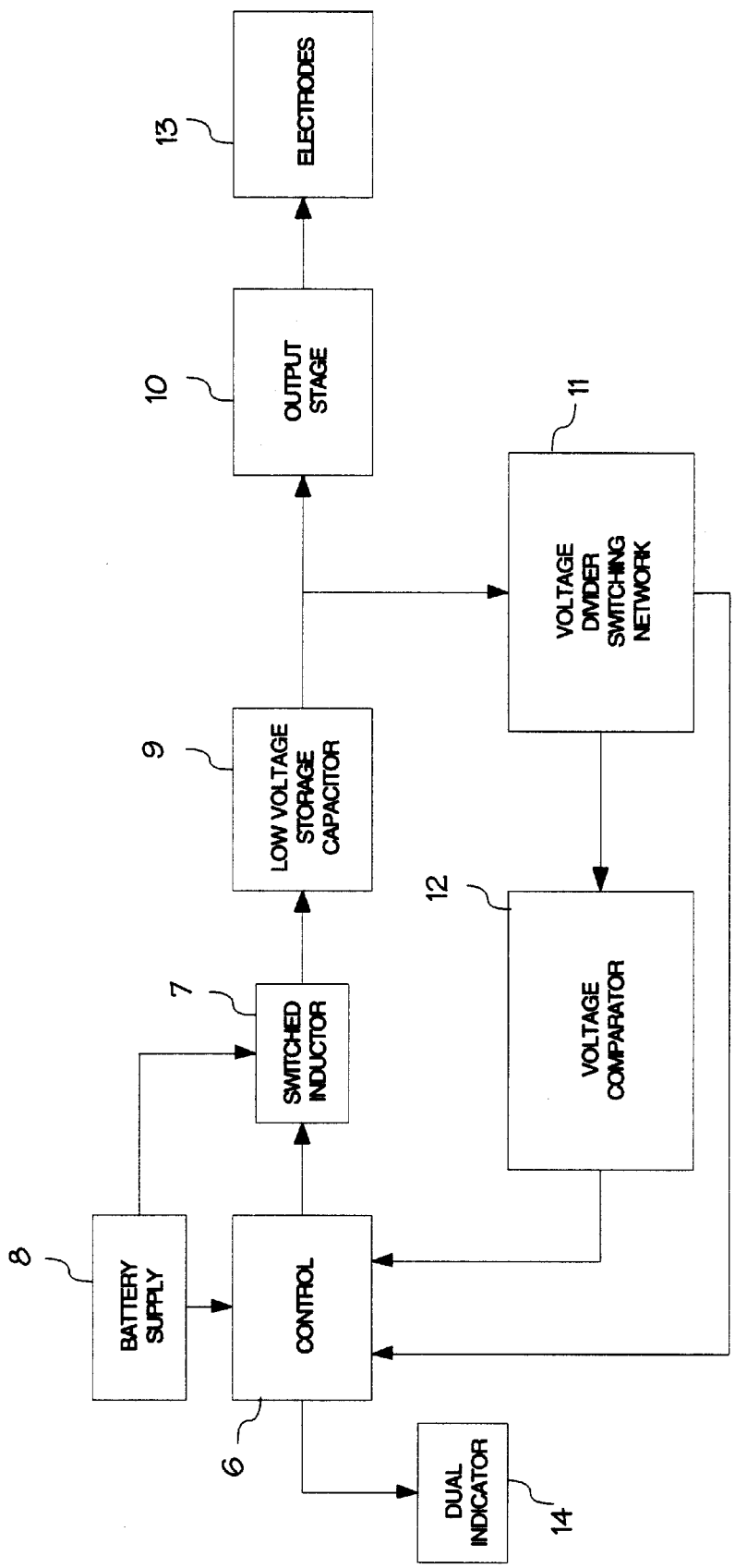
FIG. 2 is a block diagram of a pulse generator with a controlled battery draw.

FIG. 2 is a block diagram of the electrotherapy device pulse generator which accomplishes controlled battery draw as illustrated in FIG. 1b. Control module 6 connects the switched inductor 7 to the battery supply 8, generating a current draw from the battery supply 8 through the switched inductor 7 and into the low voltage storage capacitor 9. The current through the switched inductor 7 rises gradually and a voltage develops across the low voltage storage capacitor 9 due to the storage of electric charge from the current. Control 6 then disconnects the switched inductor 7 from the battery supply 8. This is called a battery discharge pulse. The switched inductor 7 then releases residual electrical current into the low voltage storage capacitor 9 causing slightly more voltage to develop across it. The low voltage storage capacitor 9 is then in an open circuit condition and holds the accumulated voltage. Repetitively causing electric current to flow through the switched inductor 7 into the storage capacitor 9 causes a voltage to build up across the storage capacitor 9 in a step-wise fashion. The capacitor functions as an intermediate storage device, and may be replaced with other forms of storage devices.

The control 6 charges the capacitor 9 until it has reached the desired intermediate output pulse voltage, and then causes the capacitor 9 to discharge into the output stage 10. To accomplish this, the control 6 must monitor the capacitor voltage. Control 6 monitors the voltage built up across the low voltage storage capacitor 9 through the voltage divider switching network 11 connected to the voltage comparator 12. Control 6 continues to operate the switched inductor 7 to build up a store of charge or current in the low voltage storage capacitor 9 until the voltage comparator 12 signals to control 6 that the corresponding voltage across the low voltage storage capacitor 9 has reached a predetermined voltage value. The voltage on the low voltage storage capacitor 9 is then delivered to the output stage 10. The output stage 10 steps up the voltage and delivers it to electrodes 13, thereby generating a therapeutic pulse through the electrodes to the patient. Various output stages may be employed. For example, where the discharge is intended for direct output to a load, the output stage may simply consist of an electrical terminal.

The predetermined voltage value is that value that has been determined to provide the optimal therapeutic pulse to the patient, and may encompass several different values. It is determined from a large number of observations and tests on patients, which indicate an optimal range of output voltages at the electrodes and a corresponding output voltage from the low voltage storage capacitor. It is measured in part based on the voltage divider switching network 11. The particular predetermined voltage and the voltage division used by the system is varied by the patient's manipulation of a switching mechanism (shown and described in FIG. 3). Thus, the predetermined voltage may be predetermined by the values of circuit components used in building the circuit, the programming of the control module, and the user's own adjustment of the device.

Control 6 limits the battery discharge pulses and time between battery discharge pulses such that the resulting average electrical current draw from the battery supply is within the battery's optimal discharge rate, i.e., low enough so as not to degrade battery performance and battery life. Narrow battery discharge pulses are preferred to limit the instantaneous electrical current draw from the battery and to be able to use small, low cost inductor components. However, a narrow battery discharge pulse requires a fast operation of the control 6, which increases power consumption the faster it is operated. The choice of inductor also determines the maximum battery discharge pulse width in order to avoid saturation of the inductor. The control 6 also needs to operate at a minimum speed in order to be able to accomplish all of its functions and still be able to deliver therapeutic pulses at the desired rate. A balance is typically found empirically between these various factors. We have found that a battery discharge pulse of approximately 4 microseconds delivered at a frequency of approximately 19.5 kilohertz is favored for 3 volt lithium/$MnO_2$ coin cell batteries used in the preferred embodiment. Other factors contribute to the electrical draw and these must be carefully considered. For example, indicators should be chosen for low electrical current requirements and should be pulsed so that their average current draw is minimized.

Control 6 also sets the battery discharge pulse width and time between battery discharge pulses so that there is sufficient time for the therapeutic pulses to be generated at the required frequency to the patient. Control 6 does this by counting the number of battery discharge pulses needed to achieve the predetermined voltage on the low voltage storage capacitor (charge pulse count), such that as the battery supply is depleted, more battery discharge pulses are ordered to be sent to the low voltage storage capacitor. The therapeutic pulses are thereby maintained while the battery supply 8 is depleted. Battery discharge pulses can be counted for each therapeutic pulse delivered. Alternatively, control could periodically attempt to charge the low voltage storage capacitor up to a maximum predetermined or arbitrary voltage as part of a calibration routine to estimate the state of the battery at predetermined intervals. This method obviates the need for the voltage divider switching network, which can then be replaced with a simple voltage divider. The pulse count can be used by a software algorithm stored in control 6 to calculate the number of pulses needed for any intermediate voltage, for example, to achieve automatic therapeutic pulse amplitude modulation. As the battery voltage declines with use, the number of charging pulses needed to achieve a particular capacitor voltage will increase, so the software algorithm must be able to accommodate this change, for example, by using different equations for different battery voltage ranges or by using various look-up tables for different battery voltage ranges. It is also possible to eliminate the need for a software algorithm through the exclusive use of look-up tables stored in additional program storage space in control 6.

When the control determines that the battery has reached a predetermined low battery value (by tracking the charge pulse count or otherwise), the control 6 changes the dual indicator 14 from a normal mode indicator to a low battery indicator and continues to deliver therapeutic pulses. The low battery value is calculated as a percentage of the total time that control can maintain the therapeutic pulses on average for the type of battery supply used. For example, if the battery supply allows control to maintain the therapeutic pulses for an average of 100 hours, the low battery value could be set at 80%, leaving the patient 20 hours of continued treatment and sufficient time to get a replacement device or battery supply.

Referring again to FIG. 1b, the capacitor charge status line indicates that, after many pulses, the battery voltage drops and more optimal pulses must be initiated to charge the capacitor to the output voltage. Eventually, the battery will discharge to a point that, no matter how many discharge pulses are initiated within the pulse period p, the battery cannot charge the capacitor to the output voltage. Thus, the voltage comparator never sees an adequate voltage; and the system controller will not initiate an output pulse from the capacitor to the transformer. Once control determines that it is unable to regulate the output due to a depleted battery supply, it stops generating therapeutic pulses to prevent a degradation of the therapeutic benefit from the device. This could be accomplished in a number of ways. Control 6 can continue to charge the low voltage storage capacitor, which will no longer output pulses to the output stage since the voltage comparator will never signal to control that the voltage across the low voltage storage capacitor has reached the predetermined voltage value. Control 6 can also repeatedly and rapidly discharge the low voltage storage capacitor 9 into the output stage 10 in order to rapidly deplete the battery 8 to the point where it cannot sustain any function. The control 6 may also continuously close Q1, leaving the battery 8 continuously connected to the switched inductor 7. Alternatively, control 6 can switch to a back up battery supply automatically to continue generation of therapeutic pulses powered by the backup battery. Furthermore, control 6 can indicate to the patient that therapeutic pulses are no longer being delivered by either turning off the indicator lights or lighting a third indicator light.

Figure 3:
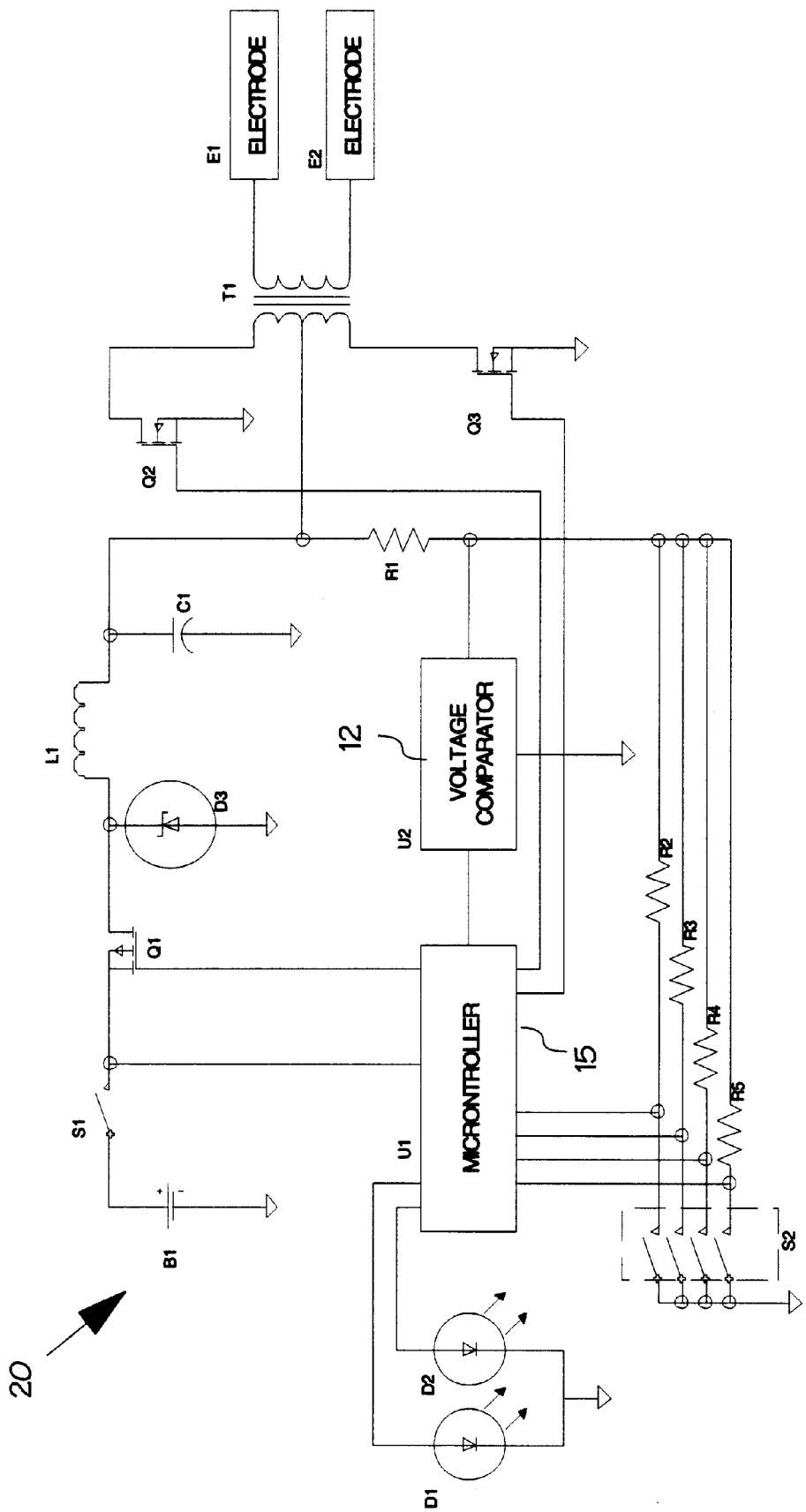
FIG. 3 is a circuit diagram of a pulse generator with a controlled battery draw.

FIG. 3 is a detailed circuit diagram of an electrotherapy device pulse controller. The circuit 20 is powered by a battery B1. The battery is selected on the basis of its battery capacity rating, which defines the maximum time that the electrotherapy device will operate. In a preferred embodiment, two CR2025 3 volt lithium coin cell batteries are connected in series (6 volts total battery supply). The average current drawn from the batteries is approximately 0.9 milliamps when delivering therapeutic pulses of 35 milliamps peak pulse amplitude (350 microsecond pulse width at 31 hertz frequency) into a simulated human skin load (500 ohm resistor). This current draw compares well to the maximum direct current draw for this type of battery, which is typically 3 milliamps. The typical battery capacity for the CR2025 is 150 milliampere-hours at a continuous electrical current draw of 0.2 milliamperes. A draw of 1 milliamp should produce somewhat less than 150 hours of battery life. Testing of the electrical circuit using two CR2025 batteries in series demonstrated that the average battery life is about 157 hours. Tests with two CR2016 coin cell batteries (70 milliampere-hour capacity) resulted in an average battery life of 87 hours under the same conditions. These results are greater than expected based on battery capacity because the device uses two coin cell batteries for a total battery supply of 6 volts, which allows the current draw to be minimized, thereby optimally draining the batteries. The total power consumed is P=V*I or approximately P=(6 V)*(0.9 mA)=5.4 milliwatts (mW). A preferred circuit can operate from a single 3 volt battery, but the current consumption must approximately double since the same amount of power is needed to deliver the therapeutic pulses. For example, the battery life of the CR2025 would be expected to be reduced from 157 hours to approximately 75 hours. Other battery types, in single or multiple cell configurations, can be selected with changes to circuit component values made accordingly.

Battery B1 is connected through switch S1 to the pulse generator circuit. Switch S1 is operable by the patient and enables the patient to turn on and off the electrotherapy device. Switch S1 is in the closed position during operation when the patient has turned on the electrotherapy device. During operation, battery B1 discharges pulses into inductor L1. Inductor L1 controls the delivery of current to capacitor C1 and reduces energy loss to maximize battery efficiency, C1 stores the electric charge and accumulates a corresponding voltage until commanded to discharge the accumulated voltage to transformer T1, whereupon T1 steps up the voltage for output to the patient in the form of therapeutic output pulses. Microcontroller 15 controls the circuit operations and comprises FIG. 2 control 6. Microcontrollers are typically characterized by their operating voltage range, their electrical current consumption, their operating speed (clock rate), the number of bits used for operations (e.g., 4 bit, 8 bit, 16 bit, etc.), the number of programmable input/output lines, software program storage space, and integrated special functions (e.g., A/D converters, high current source or sink capability, serial communication ports, etc.). Other factors include cost and availability. 4-bit and 8-bit microcontrollers are favored due to their small size, low cost, and low power consumption (e.g., Samsung KS51 series and Toshiba TLCS47 series 4-bit microcontrollers, and Samsung KS86C series, Toshiba TLCS870 series and Microchip 16C5x series 8-bit microcontrollers). A preferred embodiment uses a Microchip 16C54A 8-bit microcontroller.

Switch S1 and microcontroller 15 are connected to transistor Q1, which together with diode D3, and inductor L1 comprise FIG. 2 switched inductor 7. Microcontroller 15 connects battery B1 to the inductor L1 through transistor Q1, which microcontroller 15 operates as a switch. The microcontroller 15 repeatedly opens and closes transistor Q1 to send battery discharge pulses to inductor L1. This causes current to flow into inductor L1 and capacitor C1. Inductor L1 causes this current to increase at a controlled rate, thereby causing a voltage to develop across capacitor C1 at a controlled rate, thereby reducing energy losses. When transistor Q1 is opened, the current into inductor L1 begins to decrease. This causes the voltage across inductor L1 to reverse, thereby causing diode D3 to turn on and complete an electrical circuit between inductor L1 and capacitor C1. Residual current in inductor L1 is then allowed to flow to capacitor C1, causing its voltage to increase slightly. Once this residual current goes to zero, the inductor L1 voltage is no longer reversed and diode D3 turns off. This causes capacitor C1 to be isolated in the electrical circuit, thereby preserving the voltage stored on it. (Resistors R1 through R5 may provide a discharge path for capacitor C1 if any of the switches S2 are closed. These resistors are chosen to be high values to limit the discharge current from C1 to acceptably low values.) The value of inductor L1 is chosen to conserve battery life and provide small size and low cost. However, testing has demonstrated that inductor L1 can be replaced by a smaller, lower cost, low value resistor while still obtaining the advantage of regulated output while the battery voltage decreases with use. The drawback of this method is that, while battery life is enhanced vis-à-vis unregulated output, battery life is compromised vis-à-vis the switched inductor embodiment due to energy losses in the resistor.

Inductor L1 is connected to capacitor C1, which is chosen typically to be a high capacitance value to maximize current storage. Current flowing through inductor L1 and into capacitor C1 causes voltage to build across capacitor C1 that is proportional to the amount of current delivered over a particular time period, e.g., the battery discharge time.

Microcontroller 15 monitors the charge/voltage built up on the capacitor C1 so it knows when to stop the battery discharge pulses and/or initiate a transformer discharge pulse (therapeutic pulse). Low voltage storage capacitor C1 is connected to R1, which together with switch array S2 and resistors R2–5 comprise FIG. 2 voltage divider switching network 11. Switch array S2 is manipulated by the patient to select one of a number of available "intensity" settings. As shown in FIG. 3, switch array S2 selects one of a number of resistors in a voltage divider array formed by resistor R1 and resistors R2–5.

R1 of the voltage divider switching network is connected to voltage comparator 12. Using the voltage comparator, the microcontroller monitors the voltage across capacitor C1, and continues to allow voltage to build until voltage comparator 12 signals that the voltage has reached a predetermined voltage value.

The next step is to send a therapeutic pulse from the low voltage storage capacitor to the transformer. The low voltage storage capacitor is connected to transformer T1, which acts as the output stage 10 of FIG. 2. Transformer T1 is chosen to have a voltage step-up characteristic based on the desired therapeutic output requirements and the load connected to the electrodes E1 and E2. Once voltage across C1 has reached a predetermined value, microcontroller 15 closes either transistor Q2 or Q3 to discharge the capacitor into the transformer T1. This sends the voltage to the output stage to be stepped up by transformer T1. In a preferred embodiment, the transformer has a turns ratio of approximately 20, a low resistance primary winding (approximately 2 ohms), and a high inductance secondary winding (approximately 1 henry). The turns ratio is selected based on the maximum voltage on the storage capacitor at the primary and the desired maximum voltage delivered to the skin through the electrodes at the secondary, e.g., 3 volts at the primary can deliver 3*20=60 volts at the secondary (other factors such as transformer core saturation must be considered). The low resistance primary is needed for reduced power consumption. The high inductance secondary is needed to achieve a nominally constant current therapeutic output over a range of skin impedance values. Skin impedance changes with time for a particular patient, and can be very different between patients. A nominally constant current output allows a predictable level of therapeutic current to be delivered regardless of patient skin characteristics, thereby providing better therapeutic value.

Transistors Q2 and Q3 are needed to move electrical current through the transformer T1 primary winding in one direction or the other, thereby creating positive or negative therapeutic pulses at the electrodes E1 and E2. Preferably, the microcontroller alternately operates Q2 and Q3 to provide alternately positive and negative pulses to the electrodes. (Alternating operation of Q2 and Q3, together with the center tap 16 attachment at the center of the transformer winding, creates a polarity switching circuit which creates the alternating positive and negative voltage output from the transformer.) This prevents any iontophoretic or electropheretic effect on the patient's skin. Alternatively, transformer T1 can be replaced by a standard transformer to create single polarity pulses, or it can be removed and the inductor L1 and capacitor C1 chosen to provide the high voltage directly to the electrodes with a different switching means to effect different polarity pulses, if required. The operation of transistor Q2, Q3 and Q1 may be controlled so that the inductor L1 is always disconnected from the battery when the capacitor is discharging into the transformer. In this manner, current is supplied to the transformer only from the capacitor and not from the battery.

The circuit can also create a display to the patient. Microcontroller 15 is connected to light emitting diodes (LED) D1 and D2 which comprise FIG. 2 dual indicator. In a preferred embodiment, D1 is a green LED that is flashed at a low duty cycle to conserve battery power and is used to indicate normal operation. D2 is a red LED that is flashed at a faster rate than D1 and is used to indicate the "low battery" warning. Alternative display methods may be used including liquid crystal display, sound, vibration, etc.

Capacitor C1 can be discharged directly into the skin if certain changes are made to the circuit. Specifically, a diode can be placed in series between inductor L1 and capacitor C1, which is then chosen to be a high voltage, high capacitance component, i.e., a standard "boost" regulator configuration. The diode allows a high voltage to be stored on the capacitor from a lower voltage source. Resistor divider values are then chosen to suitably divide the peak high voltage down to a value suitable for the voltage detector. Biphasic pulses can be created using capacitor C1 as an input to a standard H-bridge transistor circuit with suitable transistors, with the electrodes connected to the middle of the H-bridge (the H-bridge is another form of polarity switching circuit). This method is not preferred because power consumption is relatively high, resulting in low battery life, and the therapeutic output becomes nominally constant voltage instead of the preferred nominally constant current achieved using a transformer or tapped inductor. However, where the H-bridge is desirable for other reasons, the battery life may be extended vis-à-vis direct connection to the battery.

The battery discharging circuit is described in connection with its use in an electrotherapy device. However, the method of discharging the battery at low average current by pulse charging a capacitive storage unit may be employed in various other environments where high current intermittent loads are powered by a battery. In one example, battery operated automobiles and carts with electric motors often stop and idle, then re-load the motor to accelerate the vehicle, thus subjecting the battery to a high current draw. This high current draw can be reduced by charging a storage capacitor through a switched inductor while idling, and discharging the capacitor into the motor electrical supply lines upon acceleration or loading of the motor. In another example, large batteries are used for starting large loads such as coolant motors and starter motors for engines. These motors typically draw a very large start-up current when they are turned on. By interposing the circuit described above between the battery and the motor during the start-up, the startup surge may be supplied from the capacitive storage device. To charge the capacitive storage device, the starter circuit for the motor would first charge the capacitive storage device, then start the motor by connecting the motor terminals to the capacitive storage device and/or the battery. In this manner, the large start-up current is drawn from the battery at a lower discharge rate than it would if the start-up current is drawn directly from the battery into the motor. In another example, a battery powered portable defibrillator uses a battery to charge a capacitor which is discharged into a patient's chest. The rate at which the capacitor charges can be controlled by placing the circuit between the battery and the capacitor. When the defibrillator is operated, the control 6 then slowly charges the capacitor with a series of relatively low current battery discharge pulses. When fully charged, the capacitor is discharged into the patient's chest in the normal fashion. In this manner, the number of defibrillating shocks that can be administered from a single battery pack is increased. In another example, the battery operated roadside safety beacons which use simple RC timing circuits can be improved by inclusion of the circuit to lower the average current draw on the battery, thereby making the battery last longer. Many other battery powered devices which intermittently draw current from the battery may be powered by the circuit to lower the instantaneous current draw and thereby lengthen battery life.

While the devices and methods have been described in reference to the environment in which they were developed, they are merely illustrative of the principles of the inventions. Other embodiments and configurations may be devised without departing from the spirit of the inventions and the scope of the appended claims.

We claim:

1. An apparatus for regulating the output in a battery powered electrotherapy device comprising:

a control means which activates a switched inductor by connecting said switched inductor to a battery supply such that the battery supply outputs a charging pulse to the switched inductor;

wherein said control means deactivates the switched inductor causing said switched inductor to deliver a charge from the switched inductor to a storage capacitor, said deactivating of the switched inductor causing voltage to build up on the storage capacitor;

wherein said control means monitors the voltage built up on the storage capacitor using a voltage divider connected to a voltage comparator until the voltage on the storage capacitor reaches a predetermined voltage at which point it delivers a capacitor discharge pulse from the storage capacitor to an output stage;

wherein said control means controls the width and frequency of the battery supply charging pulses so that battery discharge pulses are made at lower amperage than the capacitor discharge pulses; and the output stage comprises electrodes adapted to transmit electrotherapy pulses to the body of a patient.

2. An apparatus for regulating the output in a battery powered electrotherapy device comprising:

a control means which activates a switched inductor by connecting said switched inductor to a battery supply such that the battery supply outputs a charging pulse to the switched inductor;

wherein said control means deactivates the switched inductor causing said switched inductor to deliver a charge from the switched inductor to a storage capacitor, said deactivating of the switched inductor causing voltage to build up on the storage capacitor;

wherein said control means monitors the voltage built up on the storage capacitor using a voltage divider connected to a voltage comparator until the voltage on the storage capacitor reaches a predetermined voltage at which point it delivers said voltage from the storage capacitor to an output stage;

wherein said control means controls the width and frequency of the battery supply charging pulses so that battery discharge pulses are made at lower amperage than the capacitor discharge pulses;

wherein said control means counts the number of charge pulses from the battery supply needed to achieve a predetermined voltage such that as the battery supply is depleted, more charge pulses are ordered to be sent from the battery supply to the storage capacitor;

wherein said control means determines that the charge pulses count reaches a predetermined charge pulse count value equal to a predetermined percent of total value, said control means changes an indicator from normal to a low battery warning and continues to deliver therapeutic pulses, said predetermined value calculated as a percentage of the total time that the control can maintain the stimulation output on average for the type of battery supply used; and wherein said control means, once it determines that it is unable to regulate the output due to depleted battery supply, stops delivering therapeutic output pulses.

3. An apparatus for regulating the output in a battery powered electrotherapy device comprising:

a control means which activates a switched inductor by connecting said switched inductor to a battery supply such that the battery supply outputs a charging pulse to the switched inductor, thereby causing a voltage to build up on a storage capacitor;

wherein said control means deactivates the switched inductor causing said switched inductor to deliver residual charge from the switched inductor to said storage capacitor, said deactivating of the switched inductor causing additional voltage to build up on said low voltage storage capacitor;

wherein said control means monitors the voltage built up on the storage capacitor using a voltage divider connected to a voltage comparator, and the control means causes the capacitor to discharge to an output stage when the voltage on the storage capacitor reaches a predetermined voltage;

wherein said control means determines the width and frequency of the battery supply charging pulses low enough such that the resulting average electrical current draw from the battery supply is low enough to not degrade the battery performance and battery life and high enough so that there is sufficient time for the therapeutic pulses to be generated at the required frequency;

wherein said control means counts the number of charge pulses from the battery supply needed to achieve a predetermined voltage such that as the battery supply is depleted, more charge pulses are ordered to be sent from the battery supply to the storage capacitor;

wherein said control means determines that the charge pulses count reaches a predetermined charge pulse count value equal to a predetermined percent of total value, said control means changes an indicator from normal to a low battery warning and continues to deliver therapeutic pulses, said predetermined value calculated as a percentage of the total time that the control can maintain the stimulation output on average for the type of battery supply used; and wherein said control means, once it determines that it is unable to regulate the output due to a depleted battery supply, stops delivering therapeutic output pulses.

4. The device of claim 3 wherein the voltage divider is operably connected to a switch for selecting at least one voltage division setting said switch being operable by a user of the device.

5. The device of claim 3 wherein the voltage comparator transmits a signal to the control means when the voltage on the storage capacitor has reached a predetermined voltage.

6. The device of claim 3 wherein the output stage steps up the voltage and delivers it to the electrodes thereby generating a therapeutic electrical pulse to the user.

7. A device for providing a pulsed electrical stimulus to a nerve in the body of a patient, wherein said device is battery operated, said device comprising:

an electrode adapted to transmit electrotherapy pulses to the body of a patient in the vicinity of the nerve to be stimulated;

a capacitor and a first switch means for operably and intermittently connecting the capacitor to the electrode;

a battery and a second switch means operably connecting the battery to the capacitor;

control means for operating the second switch to periodically connect the battery to the capacitor, thereby transferring charge from the battery to the capacitor, and periodically connecting the capacitor to the electrode after a desired charge has been accumulated on the capacitor to apply a pulse of electrical stimulus to the nerve in the body; and a transformer interposed between the capacitor and the electrode.

8. The device of claim 7 wherein the transformer is designed to step up the voltage of the pulse of electrical stimulus and transmits a responsive pulse of electrical stimulus to the electrode, said responsive pulse of electrical stimulus being at a voltage higher than the pulse of electrical stimulus from the capacitor.

9. A method for controlling the discharge of a battery to a load, said method comprising:

providing a switched inductor, said switched inductor having an inductor input switch with an input adapted to be connected to the battery, said switched inductor having an output;

providing a capacitor adapted to be placed in circuit with the output of the inductor and collect current discharged from the inductor;

providing a capacitor output switch in circuit with the capacitor, said capacitor output switch adapted to be connected to the load;

providing a control module to control the operation of the inductor input switch and the capacitor output switch, and programming the control module to:

monitor the voltage on the storage capacitor;

operate the inductor input switch to draw a plurality of battery discharge pulses from the battery and allow the discharge pulses to cause a build up of voltage on the capacitor, and count the number of battery discharge pulses necessary to achieve a predetermined maximum voltage on the capacitor;

use the counted number of battery discharge pulses to determine the expected number of pulses necessary to achieve a predetermined desired output voltage on said storage capacitor intermediate between zero and the predetermined maximum voltage;

thereafter operate the inductor input switch to draw the expected number of battery discharge pulses from the battery to allow the discharge pulses to cause a build up of voltage on the capacitor, and operate the capacitor output switch to connect the capacitor to the load.

* * * * *